United States Patent [19]

Egger et al.

[11] Patent Number: 5,672,976
[45] Date of Patent: Sep. 30, 1997

[54] WETNESS SENSOR FOR A WINDOW OF A MOTOR VEHICLE

[75] Inventors: Armin Egger, Bad Homburg; Reinhold Berberich, Frankfurt; Dieter Busch, Rosbach, all of Germany

[73] Assignee: VDO Adolf Schindling AG, Frankfurt, Germany

[21] Appl. No.: 508,214

[22] Filed: Jul. 27, 1995

[30] Foreign Application Priority Data

Jul. 28, 1994 [DE] Germany .......................... 44 26 736.3

[51] Int. Cl.[6] .................................................. G01R 27/26
[52] U.S. Cl. .......................... 324/668; 324/689; 324/687; 340/602; 361/286; 219/203
[58] Field of Search ........................ 318/DIG. 2, 483; 361/286; 340/602; 324/687, 689, 668; 219/203

[56] References Cited

U.S. PATENT DOCUMENTS

| 4,127,763 | 11/1978 | Roselli | 318/483 |
| 4,373,392 | 2/1983 | Nagamoto | 361/286 |
| 4,820,902 | 4/1989 | Gillery | 219/203 |
| 5,040,411 | 8/1991 | Medzius | 361/286 |

Primary Examiner—Vinh P. Nguyen
Assistant Examiner—Jose M. Solis
Attorney, Agent, or Firm—Martin A. Farber

[57] ABSTRACT

In a wetness sensor for a window of a motor vehicle, a heating resistor arranged in the window and powered by DC current can be connected to a measuring device for measuring an AC impedance of the heating resistor, in particular the capacitive portion thereof. The impedance varies with the amount of wetness and, thereby, serves as a measure of the wetness. A capacitor is used to bring the sensor near resonance for improved sensitivity.

7 Claims, 1 Drawing Sheet

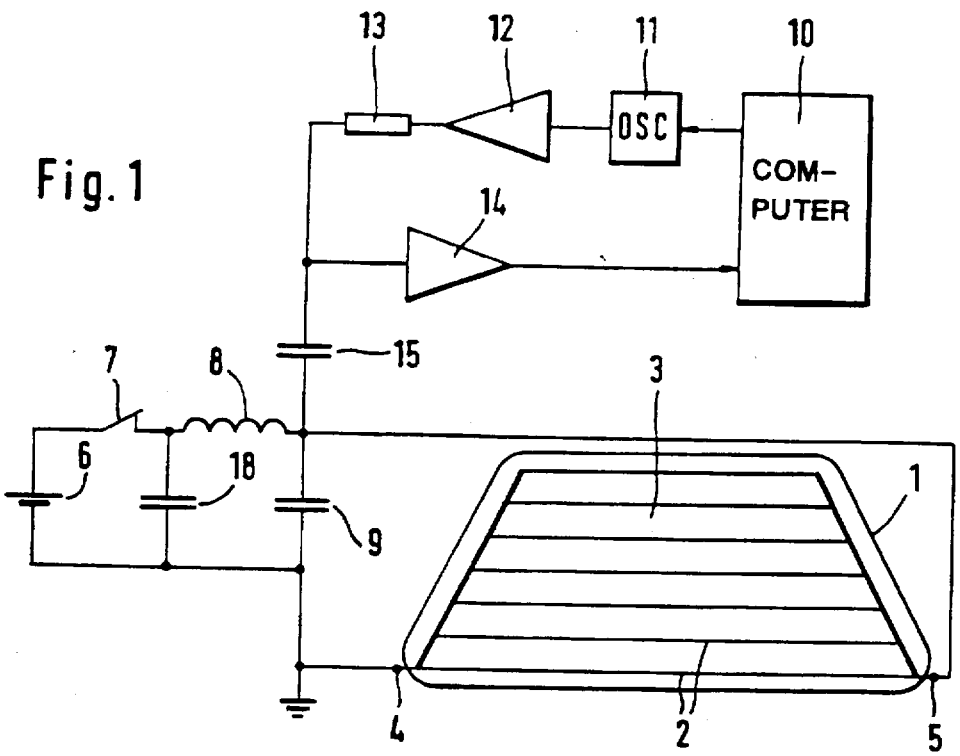
Fig.1
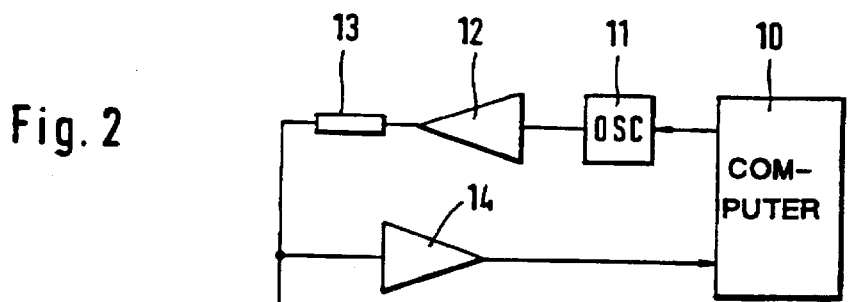
Fig.2
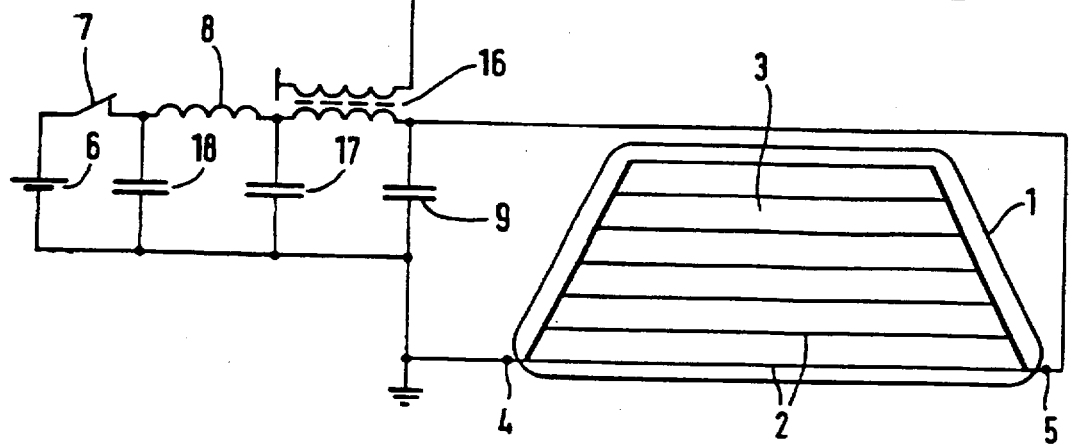

WETNESS SENSOR FOR A WINDOW OF A MOTOR VEHICLE

FIELD AND BACKGROUND OF THE INVENTION

The present invention relates to a wetness sensor for a window of a motor vehicle.

In order to control windshield wipers as a function of the amount of water on the front windshield as well as on the rear window of a motor vehicle, various sensors have become known such as resistive, capacitive, or optical sensors. In particular, resistive and capacitive sensors require electrodes which are firmly attached to the window and extend over a large area of the window if averaging of the wetness over a large area is necessary. Such electrodes, however, constitute a considerable expense.

SUMMARY OF THE INVENTION

The object of the present invention is to provide a wetness sensor with the smallest possible expense for electrodes which are to be applied to the window.

This object is achieved in accordance with the invention in the manner that a heating resistor which is present in the window can be connected to a measuring device for measuring the impedance of the heating resistor, particularly the capacitive portion of the impedance.

The wetness sensor of the invention has the advantage that a heating resistor which is already disposed on a window which is to be kept clear of frost, particularly the rear window, serves at the same time to measure the amount of water on the window. By a measurement of the impedance, and particularly the capacitive portion thereof, the degree of wetness of the window can be determined in a simple manner. For the measurement of the impedance, there is applied to the heating resistor preferably a current of high frequency, and the AC (alternating current) voltage across at the heating resistor is measured.

In accordance with a further aspect of the invention, a resonance capacitor is connected in parallel to the heating resistor. By a change in the resonance frequency with the wetness of the window, which also acts in capacitive fashion, a measurable difference of the voltage on the heating resistor between a dry window and a wet window is obtained.

The heating resistor can be easily supplied with energy for heating the resistor by connecting the heating resistor furthermore via a high-frequency choke coil to a source of direct current.

In order isolate the measuring device from the operating voltage necessary for the heating of the resistor and for the heating of the window, the heating resistor can be connected to the measuring device via a coupling capacitor or a transformer.

An automatic calibration of the wetness sensor is possible in accordance with a further feature in the manner that the high frequency current is produced by a controllable oscillator and a source of current. The frequency is varied within a predetermined range. The frequency at which the AC voltage drop across the heating resistor is the greatest or changes the fastest is stored and compared with the stored frequency which was measured with a dry window.

BRIEF DESCRIPTION OF THE DRAWINGS

With the above and other objects and advantages in view, the present invention will become more clearly understood in connection with the detailed description of preferred embodiments when considered with the accompanying drawing, of which:

FIG. 1 shows one embodiment with a measurement circuit connected to a heating resistor; and FIG. 2 shows another embodiment with an alternative mode of connection of measurement circuit to heating sensor.

Identical parts have been provided with the same reference numerals in the figures.

DETAILED DESCRIPTION OF THE PREFERRED EMBODIMENTS

In the embodiment shown in FIG. 1, wires 2 are disposed in a front window or rear window 1, the wires 2 forming a heating resistor 3. The ends of the wires 2 are connected electrically to each other and to terminals 4, 5 respectively. For the heating of the window 1, a DC (direct current) voltage is fed to the heating resistor 3 from the car battery 6 via a switch 7 and a high-frequency choke coil 8 connecting to terminal 5 of the heating resistor 3. A resonance capacitor 9 is connected in parallel to the heating resistor 3.

As measuring device there is used a microcomputer 10, a controllable oscillator 11, an amplifier 12 and a resistor 13 which together constitute a source of current, and another amplifier 14. The measuring device is connected to the terminal 5 of the heating resistor 3 via a coupling capacitor 15. The frequency of the oscillator 11 can be controlled via a control voltage produced by the microcomputer 10. The oscillator frequency covers a range around the resonance frequency which results from the capacitance of the resonance capacitor 9 and an inductance of the heating resistor 3. Since the resonance capacitor 9 and the heating resistor 3 represent a parallel tuned circuit, the input voltage of the amplifier 14 is a maximum in case of resonance, which can be noted by the microcomputer 10. The dimensioning of the resonance capacitor 9 depends essentially on the development of the heating wires 2, and the value of the capacitor 9 is chosen based on the type of vehicle.

The capacitive component of the impedance of the heating resistor 3 is increased by rain on the window 1 so that the resonance frequency is changed. This change can be used to recognize or measure the wetness. Thus, it is possible, for instance, upon a tuning of the oscillator 11, to monitor the change of voltage at the input of the amplifier 14 and, upon a predetermined rate of change, to compare the frequency then present with a frequency measured in corresponding manner with dry window during a calibrating process. A capacitor 18 provides a high-frequency short circuit which insures that any traces of high frequency current which are possibly still present can be reliably blocked off from the battery 6, regardless of the position of the switch 7.

FIG. 2 shows the further embodiment in which, instead of the coupling capacitor 15, a transformer 16 is provided, its primary winding being connected between the high-frequency choke coil 8 and the terminal 5. In order that alternating current can flow through the primary winding, the junction of the primary winding and the choke coil 8 is connected to ground potential via a capacitor 17.

The invention is not limited to the embodiments shown. For instance, the shaping of the heating wires can be adapted to the requirements of wetness sensor, and possibly optimized by the adding of further individual wires. Since such further wires which are provided in the same operation as the wires which are in any event present, no additional expense in manufacture results.

I claim:

1. A wetness sensor for a window of a motor vehicle, comprising:
    a heating resistor disposed in the window for removal of frost, said resistor comprising a grid of a plurality of wires extending across the window from a first terminal connected to a first end of each wire to a second terminal connected to a second end of each wire;
    a measuring device connected to the heating resistor via said first terminal and said second terminal for measuring a capacitive portion of an impedance of the heating resistor; and
    wherein the capacitor portion of the impedance varies in accordance with an amount of wetness of the window, thereby enabling the measuring device to sense the wetness.

2. A wetness sensor according to claim 1, wherein for the measurement of the impedance, the measuring device applies to the heating resistor an AC current and measures a resulting AC voltage developed at the heating resistor, the heating resistor being energizable by a DC current applied between said first terminal and said second terminal.

3. A wetness sensor according to claim 2, further comprising a resonance capacitor connected between said first terminal and said second terminal in parallel to the heating resistor.

4. A wetness according to claim 1, further comprising a choke coil connected to the heating resistor; and
    wherein the measuring device includes a source of direct current connected via the choke coil to the heating resistor for providing said DC current.

5. A wetness sensor according to claim 1, further comprising a coupling capacitor; and
    wherein the heating resistor is connected via one of said first and said second terminals to the measuring device via the coupling capacitor.

6. A wetness sensor according to claim 1, further comprising a transformer; and
    wherein the heating resistor is connected to the measuring device via the transformer.

7. A wetness sensor according to claim 2, wherein the measuring device comprises a computer, and an oscillator and a current source driven by the oscillator to produce the AC current for the impedance measurement, the oscillator being controllable for varying a frequency of the AC current; and
    wherein the frequency is varied in a predetermined range providing that a frequency at which an AC voltage developed across the heating resistor attains a greatest value or changes at a fastest rate is stored and compared by the computer with a stored frequency which was measured with the window in a dry condition.

* * * * *